US006458591B1

(12) United States Patent
Wyatt

(10) Patent No.: US 6,458,591 B1
(45) Date of Patent: Oct. 1, 2002

(54) ANTISENSE MODULATION OF PHOSPHORYLASE KINASE ALPHA 2 EXPRESSION

(75) Inventor: Jacqueline Wyatt, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/657,453

(22) Filed: Sep. 7, 2000

(51) Int. Cl.[7] .................. C12Q 1/68; C07H 21/04; C12N 15/85
(52) U.S. Cl. .................. 435/375; 435/6; 435/91.1; 435/325; 435/366; 536/23.1; 536/24.31; 536/24.33; 536/24.5
(58) Field of Search .................. 536/23.1, 24.1, 536/23.5, 24.5, 24.31, 24.33; 514/44; 435/320.1, 440, 455, 91.1, 325, 366

(56) References Cited

PUBLICATIONS

Douglas W. Green, MD et al., Antisense Oligonucleotides: An Evolving Technology for the Modulation of Gene Expression in Human Disease, J. Am. Coll. Surg., pp. 93–105.*
Alan M. Gewirtz et al., Facilitating oligonucleotide delivery: Helping antisense deliver on its promise, Proc. Natl. Acad. Sci. USA, vol. 93, pp. 3161–3163.*
Sudhir Agrawal, Antisense oligonucleotides: towards clinical trials, TIBTECH, Oct. 1996 (vol. 14) pp. 376–387.*
Sudhir Agrawal, Antisense therapeutics: is it as simple as simple as complementary base recognition? Molecular Medicine Today, Feb. 2000, vol. 6, pp. 72–81.*
Jutta J. Davidson et al., cDNA cloning of a liver isoform of the phosphorylase kinase a subunit and mapping of the gene to Xp22.2–p22.1, the region of human X–linked liver glycogenosis, Proc. Natl. Acad. Sci. USA, vol. 89, pp. 2096–2100.*

Jan Hendrickx et al., X–linked liver glycogenosis: localization and isolation of a candidate gene, Human Molecular Genetics, 1993, vol. 2, No. 5, pp. 583–589.*
Brushia et al., Phosphorylase kinase: the complexity of its regulation is reflected in the complexity of its structure, Front. Biosci., 1999, 4:D618–641.
Burwinkel et al., Mutation hotspots in the PHKA2 gene in X–linked liver glycogenosis due to phosphorylase kinase deficiency with atypical activity in blood cells (XLG2), Hum. Mol. Genet., 1996, 5:653–658.
Davidson et al., cDNA cloning of a liver isoform of the phosphorylase kinase alpha subunit and mapping of the gene to Xp22.2–p22.1, the region of human X– linked liver glycogenosis, Proc. Natl. Acad. Sci. U. S. A., 1992, 89:2096–2100.
Hendrickx et al., X–linked liver glycogenosis: localization and isolation of a candidate gene, Hum. Mol. Genet., 1993, 2:583–589.
Hendrickx et al., Mutations in the phosphorylase kinase gene PHKA2 are responsible for X– linked liver glycogen storage disease, Hum. Mol. Genet., 1995, 4:77–83.
Hendrickx et al., Complete genomic structure and mutational spectrum of PHKA2 in patients with x–linked liver glycogenosis type I and II, Am. J. Hum. Genet., 1999, 64:1541–1549.

* cited by examiner

Primary Examiner—John L. LeGuyader
Assistant Examiner—M Schmidt
(74) Attorney, Agent, or Firm—Licata & Tyrrell P.C.

(57) ABSTRACT

Antisense compounds, compositions and methods are provided for modulating the expression of Phosphorylase kinase alpha 2. The compositions comprise antisense compounds, particularly antisense oligonucleotides, targeted to nucleic acids encoding Phosphorylase kinase alpha 2. Methods of using these compounds for modulation of Phosphorylase kinase alpha 2 expression and for treatment of diseases associated with expression of Phosphorylase kinase alpha 2 are provided.

26 Claims, No Drawings

SEQUENCE LISTING

<160> NUMBER OF SEQ ID NOS: 105

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                    20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                    20

<210> SEQ ID NO 3
<211> LENGTH: 4566
<212> TYPE: DNA
<213> ORGANISM: Homo sapiens
<220> FEATURE:
<221> NAME/KEY: CDS
<222> LOCATION: (127)...(3834)

<400> SEQUENCE: 3

-continued

```
cggtcccatc ccaagaaccg actaaggctg tgagtgtccg ggaaccagac ccgcttggag        60
gccacagccc cgacgtcccg cgcccacgcg gcagatcggg cgctgcggcc tgggagcctc       120 gggggag atg cgg agc agg agc aat tcc ggg gtc cgc ttg gac ggg tac        168
        Met Arg Ser Arg Ser Asn Ser Gly Val Arg Leu Asp Gly Tyr
        1               5                   10 gcg cgg ctg gtg cag caa acc atc ctg tgt tac cag aat ccc gtc acg       216
Ala Arg Leu Val Gln Gln Thr Ile Leu Cys Tyr Gln Asn Pro Val Thr
15                  20                  25                  30 ggg ctg ctg tca gcc agc cat gag cag aag gat gcc tgg gtg cgg gat       264
Gly Leu Leu Ser Ala Ser His Glu Gln Lys Asp Ala Trp Val Arg Asp
                35                  40                  45 aac atc tac agt atc ctg gcc gtg tgg ggc ctg ggc atg gcc tac cgt       312
Asn Ile Tyr Ser Ile Leu Ala Val Trp Gly Leu Gly Met Ala Tyr Arg
            50                  55                  60 aag aat gca gac cgc gat gag gac aag gcc aag gcc tac gag ctg gag       360
Lys Asn Ala Asp Arg Asp Glu Asp Lys Ala Lys Ala Tyr Glu Leu Glu
        65                  70                  75 cag aac gtg gtg aag ctg atg cga ggt ctt ctc cag tgc atg atg aga       408
Gln Asn Val Val Lys Leu Met Arg Gly Leu Leu Gln Cys Met Met Arg
80                  85                  90 cag gtg gcc aaa gtg gag aag ttc aaa cac act cag agc acc aag gac       456
Gln Val Ala Lys Val Glu Lys Phe Lys His Thr Gln Ser Thr Lys Asp
95                  100                 105                 110 agc ctg cac gcc aag tac aac acc gcc acc tgt ggc acg gtg gtg ggc       504
Ser Leu His Ala Lys Tyr Asn Thr Ala Thr Cys Gly Thr Val Val Gly
                115                 120                 125 gac gac cag tgg ggc cac ctc cag gtg gat gcc acc tct ctc ttc ctc       552
Asp Asp Gln Trp Gly His Leu Gln Val Asp Ala Thr Ser Leu Phe Leu
            130                 135                 140 ctg ttc ctg gcc cag atg acc gcc tca ggc tta cgt atc att ttc act       600
Leu Phe Leu Ala Gln Met Thr Ala Ser Gly Leu Arg Ile Ile Phe Thr
        145                 150                 155 ctc gat gag gtg gcc ttc ata cag aat ctt gtc ttt tac ata gaa gct       648
Leu Asp Glu Val Ala Phe Ile Gln Asn Leu Val Phe Tyr Ile Glu Ala
160                 165                 170 gca tat aaa gtc gct gat tat gga atg tgg gag cgt gga gat aag act       696
Ala Tyr Lys Val Ala Asp Tyr Gly Met Trp Glu Arg Gly Asp Lys Thr
175                 180                 185                 190 aat cag ggc atc ccg gaa ttg aat gca agc tcc gta gga atg gcc aag       744
Asn Gln Gly Ile Pro Glu Leu Asn Ala Ser Ser Val Gly Met Ala Lys
                195                 200                 205 gca gct ctt gag gca att gat gaa ctg gac ctt ttt gga gcc cat gga       792
Ala Ala Leu Glu Ala Ile Asp Glu Leu Asp Leu Phe Gly Ala His Gly
            210                 215                 220 gga cgc aag tca gtg att cat gtt ctg cca gat gag gtc gag cac tgc       840
Gly Arg Lys Ser Val Ile His Val Leu Pro Asp Glu Val Glu His Cys
        225                 230                 235 cag tct att ctg ttc tcc atg ctg cca aga gcg tcg aca tct aaa gaa       888
Gln Ser Ile Leu Phe Ser Met Leu Pro Arg Ala Ser Thr Ser Lys Glu
240                 245                 250 att gat gct gga ctt ctt tcc att att tcc ttc ccg gcc ttt gca gtg       936
Ile Asp Ala Gly Leu Leu Ser Ile Ile Ser Phe Pro Ala Phe Ala Val
255                 260                 265                 270 gaa gat gta aac ctt gta aat gtg acc aaa aat gaa att att tct aag       984
Glu Asp Val Asn Leu Val Asn Val Thr Lys Asn Glu Ile Ile Ser Lys
                275                 280                 285 ctc cag ggg cgt tat gga tgc tgt cgc ttc ctt cga gat ggt tat aaa      1032
Leu Gln Gly Arg Tyr Gly Cys Cys Arg Phe Leu Arg Asp Gly Tyr Lys
```

|  |  |  |  |  |  |  |  |  |  |  |  |  |  |  |  |
|---|---|---|---|---|---|---|---|---|---|---|---|---|---|---|---|
|  |  | 290 |  |  |  |  | 295 |  |  |  |  | 300 |  |  |  |
| act | cca | aga | gag | gac | cct | aat | cga | ctg | cat | tat | gac | cct | gct | gaa | ctc | 1080 |
| Thr | Pro | Arg | Glu | Asp | Pro | Asn | Arg | Leu | His | Tyr | Asp | Pro | Ala | Glu | Leu |  |
|  |  | 305 |  |  |  |  | 310 |  |  |  |  | 315 |  |  |  |  |
| aag | ctc | ttc | gaa | aac | att | gaa | tgt | gag | tgg | cct | gtg | ttt | tgg | aca | tat | 1128 |
| Lys | Leu | Phe | Glu | Asn | Ile | Glu | Cys | Glu | Trp | Pro | Val | Phe | Trp | Thr | Tyr |  |
|  | 320 |  |  |  |  | 325 |  |  |  |  | 330 |  |  |  |  |  |
| ttt | ata | ata | gat | gga | gtc | ttc | agt | ggt | gat | gct | gtt | cag | gtc | caa | gaa | 1176 |
| Phe | Ile | Ile | Asp | Gly | Val | Phe | Ser | Gly | Asp | Ala | Val | Gln | Val | Gln | Glu |  |
| 335 |  |  |  |  | 340 |  |  |  |  | 345 |  |  |  |  | 350 |  |
| tac | cga | gag | gcc | ctg | gag | gga | ata | ctc | atc | aga | ggc | aag | aat | ggg | atc | 1224 |
| Tyr | Arg | Glu | Ala | Leu | Glu | Gly | Ile | Leu | Ile | Arg | Gly | Lys | Asn | Gly | Ile |  |
|  |  |  | 355 |  |  |  |  | 360 |  |  |  |  | 365 |  |  |  |
| cgc | ctg | gtg | cct | gaa | ctc | tac | gct | gtc | ccg | cct | aac | aag | gta | gat | gaa | 1272 |
| Arg | Leu | Val | Pro | Glu | Leu | Tyr | Ala | Val | Pro | Pro | Asn | Lys | Val | Asp | Glu |  |
|  |  | 370 |  |  |  |  | 375 |  |  |  |  | 380 |  |  |  |  |
| gag | tac | aag | aat | cct | cac | aca | gta | gac | cga | gtt | cct | atg | ggg | aag | gtg | 1320 |
| Glu | Tyr | Lys | Asn | Pro | His | Thr | Val | Asp | Arg | Val | Pro | Met | Gly | Lys | Val |  |
|  | 385 |  |  |  |  | 390 |  |  |  |  | 395 |  |  |  |  |  |
| cct | cat | ctg | tgg | ggc | caa | tcc | ttg | tac | atc | ctc | agc | tcg | ctg | ttg | gca | 1368 |
| Pro | His | Leu | Trp | Gly | Gln | Ser | Leu | Tyr | Ile | Leu | Ser | Ser | Leu | Leu | Ala |  |
| 400 |  |  |  |  | 405 |  |  |  |  | 410 |  |  |  |  |  |  |
| gag | gga | ttc | ctt | gcc | gct | ggt | gaa | atc | gat | ccc | tta | aat | aga | aga | ttt | 1416 |
| Glu | Gly | Phe | Leu | Ala | Ala | Gly | Glu | Ile | Asp | Pro | Leu | Asn | Arg | Arg | Phe |  |
| 415 |  |  |  |  | 420 |  |  |  |  | 425 |  |  |  |  | 430 |  |
| tcc | act | tca | gtc | aaa | cct | gat | gtt | gta | gta | caa | gtt | act | gtt | ttg | gca | 1464 |
| Ser | Thr | Ser | Val | Lys | Pro | Asp | Val | Val | Val | Gln | Val | Thr | Val | Leu | Ala |  |
|  |  |  | 435 |  |  |  |  | 440 |  |  |  |  | 445 |  |  |  |
| gaa | aac | aat | cac | att | aag | gac | tta | ttg | agg | aaa | cac | ggg | gtg | aac | gtc | 1512 |
| Glu | Asn | Asn | His | Ile | Lys | Asp | Leu | Leu | Arg | Lys | His | Gly | Val | Asn | Val |  |
|  |  | 450 |  |  |  |  | 455 |  |  |  |  | 460 |  |  |  |  |
| cag | agt | atc | gcg | gac | att | cat | cca | att | caa | gtc | cag | ccg | ggc | cgg | att | 1560 |
| Gln | Ser | Ile | Ala | Asp | Ile | His | Pro | Ile | Gln | Val | Gln | Pro | Gly | Arg | Ile |  |
|  |  | 465 |  |  |  |  | 470 |  |  |  |  | 475 |  |  |  |  |
| ctt | agt | cac | ata | tat | gcc | aag | ctt | gga | cgg | aat | aag | aat | atg | aat | ttg | 1608 |
| Leu | Ser | His | Ile | Tyr | Ala | Lys | Leu | Gly | Arg | Asn | Lys | Asn | Met | Asn | Leu |  |
|  | 480 |  |  |  |  | 485 |  |  |  |  | 490 |  |  |  |  |  |
| agt | ggg | cga | ccg | tat | cga | cat | att | ggt | gtc | ctt | gga | acc | tct | aaa | cta | 1656 |
| Ser | Gly | Arg | Pro | Tyr | Arg | His | Ile | Gly | Val | Leu | Gly | Thr | Ser | Lys | Leu |  |
| 495 |  |  |  |  | 500 |  |  |  |  | 505 |  |  |  |  | 510 |  |
| tat | gtg | att | agg | aac | caa | atc | ttt | act | ttt | aca | ccc | cag | ttc | acc | gac | 1704 |
| Tyr | Val | Ile | Arg | Asn | Gln | Ile | Phe | Thr | Phe | Thr | Pro | Gln | Phe | Thr | Asp |  |
|  |  |  | 515 |  |  |  |  | 520 |  |  |  |  | 525 |  |  |  |
| cag | cat | cac | ttc | tac | ctg | gcc | ctc | gac | aat | gag | atg | atc | gtg | gag | atg | 1752 |
| Gln | His | His | Phe | Tyr | Leu | Ala | Leu | Asp | Asn | Glu | Met | Ile | Val | Glu | Met |  |
|  |  | 530 |  |  |  |  | 535 |  |  |  |  | 540 |  |  |  |  |
| cta | agg | atc | gag | ctg | gcc | tac | ctg | tgc | acc | tgc | tgg | agg | atg | acg | ggc | 1800 |
| Leu | Arg | Ile | Glu | Leu | Ala | Tyr | Leu | Cys | Thr | Cys | Trp | Arg | Met | Thr | Gly |  |
|  |  | 545 |  |  |  |  | 550 |  |  |  |  | 555 |  |  |  |  |
| aga | ccc | aca | ctc | acc | ttc | ccc | atc | agt | cgc | acc | atg | ctc | aca | aat | gat | 1848 |
| Arg | Pro | Thr | Leu | Thr | Phe | Pro | Ile | Ser | Arg | Thr | Met | Leu | Thr | Asn | Asp |  |
|  | 560 |  |  |  |  | 565 |  |  |  |  | 570 |  |  |  |  |  |
| ggc | tca | gac | att | cat | tct | gct | gtg | ctc | tcc | aca | att | aga | aaa | cta | gag | 1896 |
| Gly | Ser | Asp | Ile | His | Ser | Ala | Val | Leu | Ser | Thr | Ile | Arg | Lys | Leu | Glu |  |
| 575 |  |  |  |  | 580 |  |  |  |  | 585 |  |  |  |  | 590 |  |
| gat | gga | tat | ttt | gga | gga | gcc | aga | gta | aaa | tta | ggg | aac | ctt | tcg | gaa | 1944 |
| Asp | Gly | Tyr | Phe | Gly | Gly | Ala | Arg | Val | Lys | Leu | Gly | Asn | Leu | Ser | Glu |  |
|  |  |  | 595 |  |  |  |  | 600 |  |  |  |  | 605 |  |  |  |
| ttt | ctc | acc | aca | tcg | ttc | tac | aca | tat | ctg | act | ttt | ctg | gat | cca | gac | 1992 |

```
                Phe Leu Thr Thr Ser Phe Tyr Thr Tyr Leu Thr Phe Leu Asp Pro Asp
                        610                 615                 620 tgt gat gag aag ttg ttt gac aat gcc agc gaa ggg act ttc agt cct       2040
Cys Asp Glu Lys Leu Phe Asp Asn Ala Ser Glu Gly Thr Phe Ser Pro
            625                 630                 635 gat agt gat tca gat ttg gta gga tat ctg gaa gac acc tgt aat caa       2088
Asp Ser Asp Ser Asp Leu Val Gly Tyr Leu Glu Asp Thr Cys Asn Gln
        640                 645                 650 gaa agc caa gac gaa ctt gac cat tat atc aac cac ctt ctg caa agc       2136
Glu Ser Gln Asp Glu Leu Asp His Tyr Ile Asn His Leu Leu Gln Ser
655                 660                 665                 670 aca tcg ttg agg tcc tat ctg cct cct ctt tgt aag aac aca gaa gac       2184
Thr Ser Leu Arg Ser Tyr Leu Pro Pro Leu Cys Lys Asn Thr Glu Asp
                675                 680                 685 cgc cat gtc ttc agt gct atc cac tcc acg cgg gac ata ctt tct gtg       2232
Arg His Val Phe Ser Ala Ile His Ser Thr Arg Asp Ile Leu Ser Val
            690                 695                 700 atg gca aaa gca aag ggt ttg gaa gtt cca ttt gtt ccc atg act ttg       2280
Met Ala Lys Ala Lys Gly Leu Glu Val Pro Phe Val Pro Met Thr Leu
        705                 710                 715 ccg act aaa gtt cta agt gcc cac cgt aaa tca ctg aat ctt gtt gat       2328
Pro Thr Lys Val Leu Ser Ala His Arg Lys Ser Leu Asn Leu Val Asp
    720                 725                 730 tct cct cag cca ctc cta gaa aag gtt cct gaa agt gac ttt cag tgg       2376
Ser Pro Gln Pro Leu Leu Glu Lys Val Pro Glu Ser Asp Phe Gln Trp
735                 740                 745                 750 ccc aga gat gac cat ggt gac gtg gac tgt gag aag ctg gtt gag cag       2424
Pro Arg Asp Asp His Gly Asp Val Asp Cys Glu Lys Leu Val Glu Gln
                755                 760                 765 cta aaa gat tgt tcg aac cta cag gac caa gca gac att ctg tac att       2472
Leu Lys Asp Cys Ser Asn Leu Gln Asp Gln Ala Asp Ile Leu Tyr Ile
            770                 775                 780 ctt tat gtc ata aag ggt ccc agc tgg gac aca aat ctc tct gga cag       2520
Leu Tyr Val Ile Lys Gly Pro Ser Trp Asp Thr Asn Leu Ser Gly Gln
        785                 790                 795 cac ggg gtc acc gtt caa aac ctt ctt ggt gag ctc tat ggg aaa gcc       2568
His Gly Val Thr Val Gln Asn Leu Leu Gly Glu Leu Tyr Gly Lys Ala
    800                 805                 810 ggc ttg aac cag gag tgg ggt ctg att cgc tac atc tca ggc ctt ctc       2616
Gly Leu Asn Gln Glu Trp Gly Leu Ile Arg Tyr Ile Ser Gly Leu Leu
815                 820                 825                 830 agg aag aaa gtg gag gtc ctg gct gag gcc tgc aca gac ctg ctt tcg       2664
Arg Lys Lys Val Glu Val Leu Ala Glu Ala Cys Thr Asp Leu Leu Ser
                835                 840                 845 cac cag aag cag ctc acc gtg ggc ctg ccg ccc gag ccc cgg gag aag       2712
His Gln Lys Gln Leu Thr Val Gly Leu Pro Pro Glu Pro Arg Glu Lys
            850                 855                 860 atc atc tct gcg ccc ctt ccc cca gag gag ctc aca aaa ctc atc tac       2760
Ile Ile Ser Ala Pro Leu Pro Pro Glu Glu Leu Thr Lys Leu Ile Tyr
        865                 870                 875 gag gcc agt ggg cag gac atc agc att gcc gtc ctc acg cag gag att       2808
Glu Ala Ser Gly Gln Asp Ile Ser Ile Ala Val Leu Thr Gln Glu Ile
    880                 885                 890 gtg gtt tac ctg gcc atg tat gtc agg gcg cag ccc agc ctc ttt gtg       2856
Val Val Tyr Leu Ala Met Tyr Val Arg Ala Gln Pro Ser Leu Phe Val
895                 900                 905                 910 gag atg ctg aga ctc cgg att gga ctg atc att cag gtg atg gcc acg       2904
Glu Met Leu Arg Leu Arg Ile Gly Leu Ile Ile Gln Val Met Ala Thr
                915                 920                 925
```

```
gag ctg gca cgg agc ctg aac tgc tca gga gaa gag gct tct gaa agt    2952
Glu Leu Ala Arg Ser Leu Asn Cys Ser Gly Glu Glu Ala Ser Glu Ser
        930                 935                 940 ttg atg aac ctc agc cct ttc gat atg aaa aat ctc ctg cac cat att    3000
Leu Met Asn Leu Ser Pro Phe Asp Met Lys Asn Leu Leu His His Ile
945                 950                 955 cta agt ggg aaa gag ttt ggc gtt gaa aga agt gtg cgc cct atc cac    3048
Leu Ser Gly Lys Glu Phe Gly Val Glu Arg Ser Val Arg Pro Ile His
    960                 965                 970 tcc tcc aca tcc agc cct acc atc tcc atc cac gag gtg ggc cat acc    3096
Ser Ser Thr Ser Ser Pro Thr Ile Ser Ile His Glu Val Gly His Thr
975                 980                 985                 990 gga gtc acc aaa act gag agg agt ggc att aac aga ctg agg agt gaa    3144
Gly Val Thr Lys Thr Glu Arg Ser Gly Ile Asn Arg Leu Arg Ser Glu
            995                 1000                1005 atg aaa cag atg act agg cgg ttt agt gct gat gaa cag ttc ttt tct    3192
Met Lys Gln Met Thr Arg Arg Phe Ser Ala Asp Glu Gln Phe Phe Ser
        1010                1015                1020 gtg ggc cag gcc gcg tcc agc agt gcg cat tcc tcc aag tct gcg agg    3240
Val Gly Gln Ala Ala Ser Ser Ser Ala His Ser Ser Lys Ser Ala Arg
    1025                1030                1035 tcc agc acc cca tcc tcg ccc act ggc acg tca tcc tca gac tcg gga    3288
Ser Ser Thr Pro Ser Ser Pro Thr Gly Thr Ser Ser Ser Asp Ser Gly
1040                1045                1050 gga cat cac atc ggc tgg ggt gag cgg cag ggc cag tgg ctg cgc agg    3336
Gly His His Ile Gly Trp Gly Glu Arg Gln Gly Gln Trp Leu Arg Arg
1055                1060                1065                1070 aga agg ctg gat ggg gcc atc aac agg gtc ccc gtg gga ttc tac cag    3384
Arg Arg Leu Asp Gly Ala Ile Asn Arg Val Pro Val Gly Phe Tyr Gln
            1075                1080                1085 agg gtg tgg aag atc ctc cag aag tgc cac ggt ctc tcc atc gat ggt    3432
Arg Val Trp Lys Ile Leu Gln Lys Cys His Gly Leu Ser Ile Asp Gly
        1090                1095                1100 tat gtc ctc cca tcc tcg acg acc cga gag atg acc ccg cat gag atc    3480
Tyr Val Leu Pro Ser Ser Thr Thr Arg Glu Met Thr Pro His Glu Ile
    1105                1110                1115 aag ttt gct gtc cat gtc gaa tcg gtg ctg aac cgc gtg ccg cag ccc    3528
Lys Phe Ala Val His Val Glu Ser Val Leu Asn Arg Val Pro Gln Pro
1120                1125                1130 gag tac cgg cag ctg ctg gtg gaa gcc atc atg gtg ctg acg ctg ctc    3576
Glu Tyr Arg Gln Leu Leu Val Glu Ala Ile Met Val Leu Thr Leu Leu
1135                1140                1145                1150 tcg gac acg gag atg acc agc atc ggg ggc atc atc cac gtg gac cag    3624
Ser Asp Thr Glu Met Thr Ser Ile Gly Gly Ile Ile His Val Asp Gln
            1155                1160                1165 atc gtg cag atg gcc agt cag ctg ttc ttg cag gac cag gtg tca att    3672
Ile Val Gln Met Ala Ser Gln Leu Phe Leu Gln Asp Gln Val Ser Ile
        1170                1175                1180 ggt gcc atg gac acc ctg gag aaa gac caa gcc aca gga atc tgc cac    3720
Gly Ala Met Asp Thr Leu Glu Lys Asp Gln Ala Thr Gly Ile Cys His
    1185                1190                1195 ttc ttt tat gac agc gct ccg agt ggg gct tat ggg acg atg acc tac    3768
Phe Phe Tyr Asp Ser Ala Pro Ser Gly Ala Tyr Gly Thr Met Thr Tyr
1200                1205                1210 cta aca aga gca gtg gct tct tat ttg cag gaa ttg ttg ccc aat tcg    3816
Leu Thr Arg Ala Val Ala Ser Tyr Leu Gln Glu Leu Leu Pro Asn Ser
1215                1220                1225                1230 ggc tgc cag atg caa tag ggtctcacct ggaaacatga tcacactctc aatctgtcac    3874
Gly Cys Gln Met Gln
            1235
```

-continued

```
gtgcccccta gccttactgg gaaccttctg tcccccaaga tccctgtgc tatcaggaaa      3934 gcatgtccca tcagaaacac tctcgggggg caatggtagc actcaccctg aaactgatgt      3994
atgttaaagc cacagagata gagctgagga gtcctgtgtt ccccgcaag gagcaccccg       4054 ggatcatttt ctaggttcat ttctctggaa catttgctgt agcatctggt ctcacggact      4114
ctgaggagga attggaaatt ggtctctttt gagtgcagag ggaactgaga cgccagctta     4174
aattggctct tgcagagagt tacagaaata gtttcgatga gctagtgaca catcctaaag    4234
atgcaaagat cctcctggcg gcagtagcct tgacaagggc cacctcttca caggatgcag    4294
tctgtctgtg caccaaactc ttcaccaaat agaacacttg tgtctctctg tggaatgggg    4354
ggttttcttg tgccttgctt gctttcatag ccttccatt tattggcatg gctgccttga     4414
tgtaacataa ttctctgtcc ccaagattta gaaaattcct cttcgttcac cttggctcat    4474
ggtcttccag ggtttttatc ctggctgtct atgaactagg gttttctcct gccttaggaa    4534
aaatactgca tcttctggaa tctagaaaaa aa                                  4566
```

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
tggaggacgc aagtcagtga                                                 20

<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5
cgacgctctt ggcagcat                                                   18

<210> SEQ ID NO 6
<211> LENGTH: 31
<212> TYPE: DNA
<213> ORGANISM: Artificial Sequence
<220> FEATURE:
<223> OTHER INFORMATION: PCR Probe

<400> SEQUENCE: 6
agatgaggtc gagcactgcc agtctattct g                                    31

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                  19

<210> SEQ ID NO 8
<211> LENGTH: 20
<212> TYPE: DNA
<213> ORGANISM: Artificial Sequence
<220> FEATURE:

```
<223> OTHER INFORMATION: PCR Primer

<400> SEQUENCE: 8
gaagatggtg atgggatttc                                                        20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                        20

<210> SEQ ID NO 10
<211> LENGTH: 390
<212> TYPE: DNA
<213> ORGANISM: Homo sapiens
<220> FEATURE:
<221> NAME/KEY: CDS
<222> LOCATION: (133)...(277)

<400> SEQUENCE: 10
gggtggattg aaacgagtac tgagcctctt gcctggcaat aaaacccag  gattagtgct            60 gacctgagtt gtcagctggt gtttccaggt aaagaaaggg tggccgttta cccagcctcc          120
tctgacttta ag ttc acc gac cag cat cac ttc tac ctg gcc ctc gac aat         171
              Phe Thr Asp Gln His His Phe Tyr Leu Ala Leu Asp Asn
                1               5                  10 gag atg atc gtg gag atg cta agg atc gag ctg gcc tac ctg tgc acc           219
Glu Met Ile Val Glu Met Leu Arg Ile Glu Leu Ala Tyr Leu Cys Thr
 15                  20                  25 tgc tgg agg atg acg ggc aga ccc aca ctc acc ttc ccc atc agt cgc           267
Cys Trp Arg Met Thr Gly Arg Pro Thr Leu Thr Phe Pro Ile Ser Arg
 30                  35                  40                  45 acc atg ctc a gtaactccag ggatttcagc aggctccctc ctgccccagg                 317
Thr Met Leu ggtggtttgg gctcttacaa atgtttaaaa tggctcccat ggccagaact aagcactgaa         377
ggggcttctt agc                                                            390

<210> SEQ ID NO 11
<211> LENGTH: 428
<212> TYPE: DNA
<213> ORGANISM: Homo sapiens
<220> FEATURE:
<221> NAME/KEY: CDS
<222> LOCATION: (139)...(297)

<400> SEQUENCE: 11
gggcagagct tggactggaa ctttggtctc cctgctccag gtcccggtcc tcatctaccc           60
tctgttagga caagcatctg ttacccaggg actgcgtgaa ggatggcact gagccatttt         120
gtgtctcttc tctaatag aat ccc gtc acg ggg ctg ctg tca gcc agc cat          171
                    Asn Pro Val Thr Gly Leu Leu Ser Ala Ser His
                      1               5                  10 gag cag aag gat gcc tgg gtg cgg gat aac atc tac agt atc ctg gcc          219
Glu Gln Lys Asp Ala Trp Val Arg Asp Asn Ile Tyr Ser Ile Leu Ala
                 15                  20                  25 gtg tgg ggc ctg ggc atg gcc tac cgt aag aat gca gac cgc gat gag          267
Val Trp Gly Leu Gly Met Ala Tyr Arg Lys Asn Ala Asp Arg Asp Glu
 30                  35                  40
```

```
gac aag gcc aag gcc tac gag ctg gag cag gtaatagtga ctgacagctg      317
Asp Lys Ala Lys Ala Tyr Glu Leu Glu Gln
         45                  50 tatctcggct gctcagccac cttctccttg aactgaaaaa cccacagaga agtagctgtg   377
tgtgcagaac tgtttgggtg taggcctctc ctctatttct gctatagaat a            428

<210> SEQ ID NO 12
<211> LENGTH: 386
<212> TYPE: DNA
<213> ORGANISM: Homo sapiens
<220> FEATURE:
<223> OTHER INFORMATION:
<221> NAME/KEY: unsure
<222> LOCATION: 30
<223> OTHER INFORMATION: unknown
<221> NAME/KEY: unsure
<222> LOCATION: 37
<223> OTHER INFORMATION: unknown
<221> NAME/KEY: unsure
<222> LOCATION: 80
<223> OTHER INFORMATION: unknown
<221> NAME/KEY: unsure
<222> LOCATION: 342
<223> OTHER INFORMATION: unknown
<221> NAME/KEY: CDS
<222> LOCATION: (94)...(262)

<400> SEQUENCE: 12
agagctctag atccaggtgg ctggctatgn ccgtganctc tgccagccat gaaccccat     60 aactatgcag agcgggcttn ccttctccct cag gtg gcc aaa gtg gag aag ttc   114
                                  Val Ala Lys Val Glu Lys Phe
                                    1               5 aaa cac act cag agc acc aag gac agc ctg cac gcc aag tac aac acc   162
Lys His Thr Gln Ser Thr Lys Asp Ser Leu His Ala Lys Tyr Asn Thr
         10                  15                  20 gcc acc tgt ggc acg gtg gtg ggc gac gac cag tgg ggc cac ctc cag   210
Ala Thr Cys Gly Thr Val Val Gly Asp Asp Gln Trp Gly His Leu Gln
 25                  30                  35 gtg gat gcc acc tct ctc ttc ctg ttc ctg gcc cag atg acc gcc       258
Val Asp Ala Thr Ser Leu Phe Leu Leu Phe Leu Ala Gln Met Thr Ala
 40                  45                  50                  55 tca g gtgagctggg gttgctggag cccattgtat aaggagtgac aatccggaaa       312
Ser aggggtggga agaggacagg tagcggccan tgtgtcaggc catgtgctgc ttcactgctt   372
taataaaata cctc                                                    386

<210> SEQ ID NO 13
<211> LENGTH: 368
<212> TYPE: DNA
<213> ORGANISM: Homo sapiens
<220> FEATURE:
<221> NAME/KEY: CDS
<222> LOCATION: (130)...(228)

<400> SEQUENCE: 13
ctggttttta aatgtgtttc attacctttg ggaaaacatg tatactagat tgcttaatga    60
aaaaggaaca ccagatattg gagtgtatgt ttattagaaa gaaaaagtaa ctcataccctg  120 tgtttgtag gca gct ctt gag gca att gat gaa ctg gac ctt ttt gga gcc  171
         Ala Ala Leu Glu Ala Ile Asp Glu Leu Asp Leu Phe Gly Ala
           1               5                  10 cat gga gga cgc aag tca gtg att cat gtt ctg cca gat gag gtc gag   219
His Gly Gly Arg Lys Ser Val Ile His Val Leu Pro Asp Glu Val Glu
 15                  20                  25                  30
```

```
cac tgc cag gtaatagcct cttgcatttc agagagcagg gaaggagagt cctggcatgg      278
His Cys Gln aaggcctggg atccagtgca gattccccac cttgctggct tggtgatact ttgcttcttt      338
gagcttcagt tttctcaccc ataaaatggg                                        368

<210> SEQ ID NO 14
<211> LENGTH: 317
<212> TYPE: DNA
<213> ORGANISM: Homo sapiens
<220> FEATURE:
<221> NAME/KEY: CDS
<222> LOCATION: (123)...(269)

<400> SEQUENCE: 14
caaagtctac tcaaaattgg caaccgtatt cgaatgttcc cttggggccg agctcatggt       60
ccctagatac tgcgcctatt agcgcatctc caggttaaac cacctctttg ttttcattc       120 ag tct att ctg ttc tcc atg ctg cca aga gcg tcg aca tct aaa gaa        167
   Ser Ile Leu Phe Ser Met Leu Pro Arg Ala Ser Thr Ser Lys Glu
     1               5                  10                  15 att gat gct gga ctt ctt tcc att att tcc ttc ccg gcc ttt gca gtg        215
Ile Asp Ala Gly Leu Leu Ser Ile Ile Ser Phe Pro Ala Phe Ala Val
            20                  25                  30 gaa gat gta aac ctt gta aat gtg acc aaa aat gaa att att tct aag        263
Glu Asp Val Asn Leu Val Asn Val Thr Lys Asn Glu Ile Ile Ser Lys
        35                  40                  45 ctc cag gtaagcatta gtcatgctgg tgccttctg tcctgtgtcg atgtgcat            317
Leu Gln <210> SEQ ID NO 15
<211> LENGTH: 311
<212> TYPE: DNA
<213> ORGANISM: Homo sapiens
<220> FEATURE:
<221> NAME/KEY: CDS
<222> LOCATION: (126)...(179)

<400> SEQUENCE: 15
agcaaagaac acttggtata aaattcatta ctaaagatt catgggaaag agggtgcagg       60
gctgacttga attaaaaagg caaaaaaatt tctctgagct catcgaatgt actttctctt     120 attag ggg cgt tat gga tgc tgt cgc ttc ctt cga gat ggt tat aaa act     170
      Gly Arg Tyr Gly Cys Cys Arg Phe Leu Arg Asp Gly Tyr Lys Thr
        1               5                  10                  15 cca aga gag gttgtattta aatattgttt cttatctttc ctcaactgtt tcatctctaa    229
Pro Arg Glu gttgccaatg tgttgttctc cctctgctga ttataatttt atgttggaat attggaaagg     289
gaatattaat tttggagtca gc                                               311

<210> SEQ ID NO 16
<211> LENGTH: 378
<212> TYPE: DNA
<213> ORGANISM: Homo sapiens
<220> FEATURE:
<221> NAME/KEY: CDS
<222> LOCATION: (129)...(251)

<400> SEQUENCE: 16
taaaatccta tcatgccaa cttcaaagct gtaaaaatca gtcaagcatg ggaaaccca        60 tgaggcacaa tggtattatg tatgtattct gacatcacct tttaaaagtt tgacttattt     120 gattctag gac cct aat cga ctg cat tat gac cct gct gaa ctc aag ctc      170
```

```
            Asp Pro Asn Arg Leu His Tyr Asp Pro Ala Glu Leu Lys Leu
              1               5                  10 ttc gaa aac att gaa tgt gag tgg cct gtg ttt tgg aca tat ttt ata         218
Phe Glu Asn Ile Glu Cys Glu Trp Pro Val Phe Trp Thr Tyr Phe Ile
 15              20                  25                  30 ata gat gga gtc ttc agt ggt gat gct gtt cag gtgagaaaat gctgggtgtt      271
Ile Asp Gly Val Phe Ser Gly Asp Ala Val Gln
             35                  40 acgttgataa ttattttcat tccactggta tactgattat tattagaaca tagggttatg      331
caagaattta ggtcactgtt tcggttatct gttcccactt agcaaac                    378

<210> SEQ ID NO 17
<211> LENGTH: 4392
<212> TYPE: DNA
<213> ORGANISM: Homo sapiens
<220> FEATURE:
<221> NAME/KEY: CDS
<222> LOCATION: (172)...(3879)

<400> SEQUENCE: 17
ggactttggg gctagcgttt agaaaagtct cgacctcctc cggcccggtc ccatcccaag       60
aaccgactaa ggctgtgagt gtccgggaac cagaccogct tggaggccac agccccgacg      120
tcccgcgccc acgcggcaga tcgggcgctg cggcctggga gcctcgggga g atg cgg      177
                                                          Met Arg
                                                            1 agc agg agc aat tcc ggg gtc cgc ttg gac ggg tac gcg cgg ctg gtg       225
Ser Arg Ser Asn Ser Gly Val Arg Leu Asp Gly Tyr Ala Arg Leu Val
      5                  10                  15 cag caa acc atc ctg tgt tac cag aat ccc gtc acg ggg ctg ctg tca       273
Gln Gln Thr Ile Leu Cys Tyr Gln Asn Pro Val Thr Gly Leu Leu Ser
 20                  25                  30 gcc agc cat gag cag aag gat gcc tgg gtg cgg gat aac atc tac agt       321
Ala Ser His Glu Gln Lys Asp Ala Trp Val Arg Asp Asn Ile Tyr Ser
 35                  40                  45                  50 atc ctg gcc gtg tgg ggc ctg ggc atg gcc tac cgt aag aat gca gac       369
Ile Leu Ala Val Trp Gly Leu Gly Met Ala Tyr Arg Lys Asn Ala Asp
             55                  60                  65 cgc gat gag gac aag gcc aag gcc tac gag ctg gag cag aac gtg gtg       417
Arg Asp Glu Asp Lys Ala Lys Ala Tyr Glu Leu Glu Gln Asn Val Val
             70                  75                  80 aag ctg atg cga ggt ctt ctc cag tgc atg atg aga cag gtg gcc aaa       465
Lys Leu Met Arg Gly Leu Leu Gln Cys Met Met Arg Gln Val Ala Lys
         85                  90                  95 gtg gag aag ttc aaa cac act cag agc acc aag gac agc ctg cac gcc       513
Val Glu Lys Phe Lys His Thr Gln Ser Thr Lys Asp Ser Leu His Ala
     100                 105                 110 aag tac aac acc gcc acc tgt ggc acg gtg gtg ggc gac gac cag tgg       561
Lys Tyr Asn Thr Ala Thr Cys Gly Thr Val Val Gly Asp Asp Gln Trp
115                 120                 125                 130 ggc cac ctc cag gtg gat gcc acc tct ctc ttc ctc ctg ttc ctg gcc       609
Gly His Leu Gln Val Asp Ala Thr Ser Leu Phe Leu Leu Phe Leu Ala
             135                 140                 145 cag atg acc gcc tca ggc tta cgt atc att ttc act ctc gat gag gtg       657
Gln Met Thr Ala Ser Gly Leu Arg Ile Ile Phe Thr Leu Asp Glu Val
         150                 155                 160 gcc ttc ata cag aat ctt gtc ttt tac ata gaa gct gca tat aaa gtc       705
Ala Phe Ile Gln Asn Leu Val Phe Tyr Ile Glu Ala Ala Tyr Lys Val
     165                 170                 175 gct gat tat gga atg tgg gag cgt gga gat aag act aat cag ggc atc       753
```

-continued

```
Ala Asp Tyr Gly Met Trp Glu Arg Gly Asp Lys Thr Asn Gln Gly Ile
    180                 185                 190 ccg gaa ttg aat gca agc tcc gta gga atg gcc aag gca gct ctt gag      801
Pro Glu Leu Asn Ala Ser Ser Val Gly Met Ala Lys Ala Ala Leu Glu
195                 200                 205                 210 gca att gat gaa ctg gac ctt ttt gga gcc cat gga gga cgc aag tca      849
Ala Ile Asp Glu Leu Asp Leu Phe Gly Ala His Gly Gly Arg Lys Ser
                215                 220                 225 gtg att cat gtt ctg cca gat gag gtc gag cac tgc cag tct att ctg      897
Val Ile His Val Leu Pro Asp Glu Val Glu His Cys Gln Ser Ile Leu
            230                 235                 240 ttc tcc atg ctg cca aga gcg tcg aca tct aaa gaa att gat gct gga      945
Phe Ser Met Leu Pro Arg Ala Ser Thr Ser Lys Glu Ile Asp Ala Gly
        245                 250                 255 ctt ctt tcc att att tcc ttc ccg gcc ttt gca gtg gaa gat gta aac      993
Leu Leu Ser Ile Ile Ser Phe Pro Ala Phe Ala Val Glu Asp Val Asn
    260                 265                 270 ctt gta aat gtg acc aaa aat gaa att att tct aag ctc cag ggg cgt     1041
Leu Val Asn Val Thr Lys Asn Glu Ile Ile Ser Lys Leu Gln Gly Arg
275                 280                 285                 290 tat gga tgc tgt cgc ttc ctt cga gat ggt tat aaa act cca aga gag     1089
Tyr Gly Cys Cys Arg Phe Leu Arg Asp Gly Tyr Lys Thr Pro Arg Glu
                295                 300                 305 gac cct aat cga ctg cat tat gac cct gct gaa ctc aag ctc ttc gaa     1137
Asp Pro Asn Arg Leu His Tyr Asp Pro Ala Glu Leu Lys Leu Phe Glu
            310                 315                 320 aac att gaa tgt gag tgg cct gtg ttt tgg aca tat ttt ata ata gat     1185
Asn Ile Glu Cys Glu Trp Pro Val Phe Trp Thr Tyr Phe Ile Ile Asp
        325                 330                 335 gga gtc ttc agt ggt gat gct gtt cag gtc caa gaa tac cga gag gcc     1233
Gly Val Phe Ser Gly Asp Ala Val Gln Val Gln Glu Tyr Arg Glu Ala
    340                 345                 350 ctg gag gga ata ctc atc aga ggc aag aat ggg atc cgc ctg gtg cct     1281
Leu Glu Gly Ile Leu Ile Arg Gly Lys Asn Gly Ile Arg Leu Val Pro
355                 360                 365                 370 gaa ctc tac gct gtc ccg cct aac aag gta gat gaa gag tac aag aat     1329
Glu Leu Tyr Ala Val Pro Pro Asn Lys Val Asp Glu Glu Tyr Lys Asn
                375                 380                 385 cct cac aca gta gac cga gtt cct atg ggg aag gtg cct cat ctg tgg     1377
Pro His Thr Val Asp Arg Val Pro Met Gly Lys Val Pro His Leu Trp
            390                 395                 400 ggc caa tcc ttg tac atc ctc agc tcg ctg ttg gca gag gga ttc ctt     1425
Gly Gln Ser Leu Tyr Ile Leu Ser Ser Leu Leu Ala Glu Gly Phe Leu
        405                 410                 415 gcc gct ggt gaa atc gat ccc tta aat aga aga ttt tcc act tca gtc     1473
Ala Ala Gly Glu Ile Asp Pro Leu Asn Arg Arg Phe Ser Thr Ser Val
    420                 425                 430 aaa cct gat gtt gta gta caa gtt act gtt ttg gca gaa aac aat cac     1521
Lys Pro Asp Val Val Val Gln Val Thr Val Leu Ala Glu Asn Asn His
435                 440                 445                 450 att aag gac tta ttg agg aaa cac ggg gtg aac gtc cag agt atc gcg     1569
Ile Lys Asp Leu Leu Arg Lys His Gly Val Asn Val Gln Ser Ile Ala
                455                 460                 465 gac att cat cca att caa gtc cag ccg ggc cgg att ctt agt cac ata     1617
Asp Ile His Pro Ile Gln Val Gln Pro Gly Arg Ile Leu Ser His Ile
            470                 475                 480 tat gcc aag ctt gga cgg aat aag aat atg aat ttg agt ggg cga ccg     1665
Tyr Ala Lys Leu Gly Arg Asn Lys Asn Met Asn Leu Ser Gly Arg Pro
        485                 490                 495
```

```
tat cga cat att ggt gtc ctt gga acc tct aaa cta tat gtg att agg       1713
Tyr Arg His Ile Gly Val Leu Gly Thr Ser Lys Leu Tyr Val Ile Arg
500                 505                 510 aac caa atc ttt act ttt aca ccc cag ttc acc gac cag cat cac ttc       1761
Asn Gln Ile Phe Thr Phe Thr Pro Gln Phe Thr Asp Gln His His Phe
515                 520                 525                 530 tac ctg gcc ctc gac aat gag atg atc gtg gag atg cta agg atc gag       1809
Tyr Leu Ala Leu Asp Asn Glu Met Ile Val Glu Met Leu Arg Ile Glu
            535                 540                 545 ctg gcc tac ctg tgc acc tgc tgg agg atg acg ggc aga ccc aca ctc       1857
Leu Ala Tyr Leu Cys Thr Cys Trp Arg Met Thr Gly Arg Pro Thr Leu
550                 555                 560 acc ttc ccc atc agt cgc acc atg ctc aca aat gat ggc tca gac att       1905
Thr Phe Pro Ile Ser Arg Thr Met Leu Thr Asn Asp Gly Ser Asp Ile
            565                 570                 575 cat tct gct gtg ctc tcc aca att aga aaa cta gag gat gga tat ttt       1953
His Ser Ala Val Leu Ser Thr Ile Arg Lys Leu Glu Asp Gly Tyr Phe
580                 585                 590 gga gga gcc aga gta aaa tta ggg aac ctt tcg gaa ttt ctc acc aca       2001
Gly Gly Ala Arg Val Lys Leu Gly Asn Leu Ser Glu Phe Leu Thr Thr
595                 600                 605                 610 tcg ttc tac aca tat ctg act ttt ctg gat cca gac tgt gat gag aag       2049
Ser Phe Tyr Thr Tyr Leu Thr Phe Leu Asp Pro Asp Cys Asp Glu Lys
            615                 620                 625 ttg ttt gac aat gcc agc gaa ggg act ttc agt cct gat agt gat tca       2097
Leu Phe Asp Asn Ala Ser Glu Gly Thr Phe Ser Pro Asp Ser Asp Ser
            630                 635                 640 gat ttg gta gga tat ctg gaa gac acc tgt aat caa gaa agc caa gac       2145
Asp Leu Val Gly Tyr Leu Glu Asp Thr Cys Asn Gln Glu Ser Gln Asp
            645                 650                 655 gaa ctt gac cat tat atc aac cac ctt ctg caa agc aca tcg ttg agg       2193
Glu Leu Asp His Tyr Ile Asn His Leu Leu Gln Ser Thr Ser Leu Arg
660                 665                 670 tcc tat ctg cct cct ctt tgt aag aac aca gaa gac cgc cat gtc ttc       2241
Ser Tyr Leu Pro Pro Leu Cys Lys Asn Thr Glu Asp Arg His Val Phe
675                 680                 685                 690 agt gct atc cac tcc acg cgg gac ata ctt tct gtg atg gca aaa gca       2289
Ser Ala Ile His Ser Thr Arg Asp Ile Leu Ser Val Met Ala Lys Ala
            695                 700                 705 aag ggt ttg gaa gtt cca ttt gtt ccc atg act ttg ccg act aaa gtt       2337
Lys Gly Leu Glu Val Pro Phe Val Pro Met Thr Leu Pro Thr Lys Val
            710                 715                 720 cta agt gcc cac cgt aaa tca ctg aat ctt gtt gat tct cct cag cca       2385
Leu Ser Ala His Arg Lys Ser Leu Asn Leu Val Asp Ser Pro Gln Pro
            725                 730                 735 ctc cta gaa aag gtt cct gaa agt gac ttt cag tgg ccc aga gat gac       2433
Leu Leu Glu Lys Val Pro Glu Ser Asp Phe Gln Trp Pro Arg Asp Asp
740                 745                 750 cat ggt gac gtg gac tgt gag aag ctg gtt gag cag cta aaa gat tgt       2481
His Gly Asp Val Asp Cys Glu Lys Leu Val Glu Gln Leu Lys Asp Cys
755                 760                 765                 770 tcg aac cta cag gac caa gca gac att ctg tac att ctt tat gtc ata       2529
Ser Asn Leu Gln Asp Gln Ala Asp Ile Leu Tyr Ile Leu Tyr Val Ile
            775                 780                 785 aag ggt ccc agc tgg gac aca aat ctc tct gga cag cac ggg gtc acc       2577
Lys Gly Pro Ser Trp Asp Thr Asn Leu Ser Gly Gln His Gly Val Thr
            790                 795                 800 gtt caa aac ctt ctt ggt gag ctc tat ggg aaa gcc ggc ttg aac cag       2625
Val Gln Asn Leu Leu Gly Glu Leu Tyr Gly Lys Ala Gly Leu Asn Gln
805                 810                 815
```

```
gag tgg ggt ctg att cgc tac atc tca ggc ctt ctc agg aag aaa gtg       2673
Glu Trp Gly Leu Ile Arg Tyr Ile Ser Gly Leu Leu Arg Lys Lys Val
    820                 825                 830 gag gtc ctg gct gag gcc tgc aca gac ctg ctt tcg cac cag aag cag       2721
Glu Val Leu Ala Glu Ala Cys Thr Asp Leu Leu Ser His Gln Lys Gln
835                 840                 845                 850 ctc acc gtg ggc ctg ccg ccc gag ccc cgg gag aag atc atc tct gcg       2769
Leu Thr Val Gly Leu Pro Pro Glu Pro Arg Glu Lys Ile Ile Ser Ala
                855                 860                 865 ccc ctt ccc cca gag gag ctc aca aaa ctc atc tac gag gcc agt ggg       2817
Pro Leu Pro Pro Glu Glu Leu Thr Lys Leu Ile Tyr Glu Ala Ser Gly
        870                 875                 880 cag gac atc agc att gcc gtc ctc acg cag gag att gtg gtt tac ctg       2865
Gln Asp Ile Ser Ile Ala Val Leu Thr Gln Glu Ile Val Val Tyr Leu
            885                 890                 895 gcc atg tat gtc agg gcg cag ccc agc ctc ttt gtg gag atg ctg aga       2913
Ala Met Tyr Val Arg Ala Gln Pro Ser Leu Phe Val Glu Met Leu Arg
    900                 905                 910 ctc cgg att gga ctg atc att cag gtg atg gcc acg gag ctg gca cgg       2961
Leu Arg Ile Gly Leu Ile Ile Gln Val Met Ala Thr Glu Leu Ala Arg
915                 920                 925                 930 agc ctg aac tgc tca gga gaa gag gct tct gaa agt ttg atg aac ctc       3009
Ser Leu Asn Cys Ser Gly Glu Glu Ala Ser Glu Ser Leu Met Asn Leu
                935                 940                 945 agc cct ttc gat atg aaa aat ctc ctg cac cat att cta agt ggg aaa       3057
Ser Pro Phe Asp Met Lys Asn Leu Leu His His Ile Leu Ser Gly Lys
        950                 955                 960 gag ttt ggc gtt gaa aga agt gtg cgc cct atc cac tcc tcc aca tcc       3105
Glu Phe Gly Val Glu Arg Ser Val Arg Pro Ile His Ser Ser Thr Ser
            965                 970                 975 agc cct acc atc tcc atc cac gag gtg ggc cat acc gga gtc acc aaa       3153
Ser Pro Thr Ile Ser Ile His Glu Val Gly His Thr Gly Val Thr Lys
    980                 985                 990 act gag agg agt ggc att aac aga ctg agg agt gaa atg aaa cag atg       3201
Thr Glu Arg Ser Gly Ile Asn Arg Leu Arg Ser Glu Met Lys Gln Met
995                 1000                1005                1010 act agg cgg ttt agt gct gat gaa cag ttc ttt tct gtg ggc cag gcc       3249
Thr Arg Arg Phe Ser Ala Asp Glu Gln Phe Phe Ser Val Gly Gln Ala
                1015                1020                1025 gcg tcc agc agt gcg cat tcc tcc aag tct gcg agg tcc agc acc cca       3297
Ala Ser Ser Ser Ala His Ser Ser Lys Ser Ala Arg Ser Ser Thr Pro
        1030                1035                1040 tcc tcg ccc act ggc acg tca tcc tca gac tcg gga gga cat cac atc       3345
Ser Ser Pro Thr Gly Thr Ser Ser Ser Asp Ser Gly Gly His His Ile
            1045                1050                1055 ggc tgg ggt gag cgg cag ggc cag tgg ctg cgc agg aga agg ctg gat       3393
Gly Trp Gly Glu Arg Gln Gly Gln Trp Leu Arg Arg Arg Arg Leu Asp
    1060                1065                1070 ggg gcc atc aac agg gtc ccc gtg gga ttc tac cag agg gtg tgg aag       3441
Gly Ala Ile Asn Arg Val Pro Val Gly Phe Tyr Gln Arg Val Trp Lys
1075                1080                1085                1090 atc ctc cag aag tgc cac ggt ctc tcc atc gat ggt tat gtc ctc cca       3489
Ile Leu Gln Lys Cys His Gly Leu Ser Ile Asp Gly Tyr Val Leu Pro
                1095                1100                1105 tcc tcg acg acc cga gag atg acc ccg cat gag atc aag ttt gct gtc       3537
Ser Ser Thr Thr Arg Glu Met Thr Pro His Glu Ile Lys Phe Ala Val
        1110                1115                1120 cat gtc gaa tcg gtg ctg aac cgc gtg ccg cag ccc gag tac cgg cag       3585
His Val Glu Ser Val Leu Asn Arg Val Pro Gln Pro Glu Tyr Arg Gln
```

```
ctg ctg gtg gaa gcc atc atg gtg ctg acg ctg ctc tcg gac acg gag    3633
Leu Leu Val Glu Ala Ile Met Val Leu Thr Leu Leu Ser Asp Thr Glu
    1140                1145                1150 atg acc agc atc ggg ggc atc atc cac gtg gac cag atc gtg cag atg    3681
Met Thr Ser Ile Gly Gly Ile Ile His Val Asp Gln Ile Val Gln Met
1155                1160                1165                1170 gcc agt cag ctg ttc ttg cag gac cag gtg tca att ggt gcc atg gac    3729
Ala Ser Gln Leu Phe Leu Gln Asp Gln Val Ser Ile Gly Ala Met Asp
                1175                1180                1185 acc ctg gag aaa gac caa gcc aca gga atc tgc cac ttc ttt tat gac    3777
Thr Leu Glu Lys Asp Gln Ala Thr Gly Ile Cys His Phe Phe Tyr Asp
            1190                1195                1200 agc gct ccg agt ggg gct tat ggg acg atg acc tac cta aca aga gca    3825
Ser Ala Pro Ser Gly Ala Tyr Gly Thr Met Thr Tyr Leu Thr Arg Ala
        1205                1210                1215 gtg gct tct tat ttg cag gaa ttg ttg ccc aat tcg ggc tgc cag atg    3873
Val Ala Ser Tyr Leu Gln Glu Leu Leu Pro Asn Ser Gly Cys Gln Met
    1220                1225                1230 caa tag ggtctcacct ggaaacatga tcacactctc aatctgtcac gtgcccccta    3929
Gln
1235 gccttactgg gaaccttctg tcccccaaga tccctgtgc tatcaggaaa gcatgtccca    3989 tcagaaacac tctcgggggg caatggtagc actcaccctg aaactgatgt atgttaaagc    4049 cacagagata gagctgagga gtcctgtgtt ccccgcaag gagcacccg ggatcatttt    4109 ctaggttcat ttctctggaa catttgctgt agcatctggt ctcacggact ctgaggagga    4169 attggaaatt ggtctctttt gagtgcagag ggaactgaga cgccagctta aattggctct    4229 tgcagagagt tacagaaata gtttcgatga gctagtgaca catcctaaag atgcaaagat    4289 cctcctggcg gcagtagcct tgacaagggc cacctcttca caggatgcag tctgtctgtg    4349 caccaaactc ttcaccaaat agaacacttg tgtctctctg tgg                     4392

<210> SEQ ID NO 18
<211> LENGTH: 342
<212> TYPE: DNA
<213> ORGANISM: Homo sapiens
<220> FEATURE:
<221> NAME/KEY: CDS
<222> LOCATION: (118)...(252)

<400> SEQUENCE: 18
gttttactgc atcgctgatg tgtatgtcac caggcagaag agggcagtaa ggaacacgtg     60
tccatgtgaa gagacaagag tcatgagcta acgctcattc tgtgttcttg ttcacag       117 tta ctg ttt tgg cag aaa aca atc aca tta agg act tat tga gga aac     165
Leu Leu Phe Trp Gln Lys Thr Ile Thr Leu Arg Thr Tyr     Gly Asn
1               5                   10                      15 acg ggg tga acg tcc aga gta tcg cgg aca ttc atc caa ttc aag tcc     213
Thr Gly     Thr Ser Arg Val Ser Arg Thr Phe Ile Gln Phe Lys Ser
            20                  25                  30 agc cgg gcc gga ttc tta gtc aca tat atg cca agc ttg gtaggtttgg     262
Ser Arg Ala Gly Phe Leu Val Thr Tyr Met Pro Ser Leu
        35                  40                  45 ggaaattacc tgggcctttt tggcatgggg gcatctcggt tctagatttg gggtctgagg    322
gagactgtga tatacgtaag                                                342
```

```
<210> SEQ ID NO 19
<211> LENGTH: 332
<212> TYPE: DNA
<213> ORGANISM: Homo sapiens
<220> FEATURE:
<221> NAME/KEY: CDS
<222> LOCATION: (74)...(274)

<400> SEQUENCE: 19
ggttactcgg tgattgattg atagggctgc atctgtcctc tcactggtgg ttgcctgcct      60 gtcccttttgg tag atg acc ccg cat gag atc aag ttt gct gtc cat gtc      109
             Met Thr Pro His Glu Ile Lys Phe Ala Val His Val
               1               5                  10 gaa tcg gtg ctg aac cgc gtg ccg cag ccc gag tac cgg cag ctg ctg      157
Glu Ser Val Leu Asn Arg Val Pro Gln Pro Glu Tyr Arg Gln Leu Leu
         15                  20                  25 gtg gaa gcc atc atg gtg ctg acg ctg ctc tcg gac acg gag atg acc      205
Val Glu Ala Ile Met Val Leu Thr Leu Leu Ser Asp Thr Glu Met Thr
 30                  35                  40 agc atc ggg ggc atc atc cac gtg gac cag atc gtg cag atg gcc agt      253
Ser Ile Gly Gly Ile Ile His Val Asp Gln Ile Val Gln Met Ala Ser
 45                  50                  55                  60 cag ctg ttc ttg cag gac cag gtgggggtgc agggagctg ggttggctgg          304
Gln Leu Phe Leu Gln Asp Gln
                 65 catttatctc tgttgaggct ggagattc                                        332

<210> SEQ ID NO 20
<211> LENGTH: 400
<212> TYPE: DNA
<213> ORGANISM: Homo sapiens
<220> FEATURE:
<221> NAME/KEY: CDS
<222> LOCATION: (90)...(263)

<400> SEQUENCE: 20
agtgcgtctt gctgcccatg gtcactattg tgtagtcata tttctacagc ttggtttcat      60
tggctctttt tcttcttgtc caattacag aaa gcc aag acg aac ttg acc att      113
                                Lys Ala Lys Thr Asn Leu Thr Ile
                                  1               5 ata tca acc acc ttc tgc aaa gca cat cgt tga ggt cct atc tgc ctc      161
Ile Ser Thr Thr Phe Cys Lys Ala His Arg     Gly Pro Ile Cys Leu
 10                  15                          20 ctc ttt gta aga aca cag aag acc gcc atg tct tca gtg cta tcc act      209
Leu Phe Val Arg Thr Gln Lys Thr Ala Met Ser Ser Val Leu Ser Thr
 25                  30                  35                  40 cca cgc ggg aca tac ttt ctg tga tgg caa aag caa agg gtt tgg aag      257
Pro Arg Gly Thr Tyr Phe Leu     Trp Gln Lys Gln Arg Val Trp Lys
                 45                  50                  55 ttc cat gtatgttatt aactcttttc tgcctgttaa ataccttct tttatcaaag         313
Phe His taatgcaggg acataattta aaagccaaag aatcctagaa gacaacaaaa tgcccccac      373 gtgcttctac ttagaggtaa ccactttt                                        400

<210> SEQ ID NO 21
<211> LENGTH: 322
<212> TYPE: DNA
<213> ORGANISM: Homo sapiens
<220> FEATURE:
<221> NAME/KEY: CDS
<222> LOCATION: (150)...(229)
```

```
<400> SEQUENCE: 21
tttttcagat caagggcaac atgggtcact aagtttgtaa aggtaaatgt acgatctgat      60
tggcagtgtc tcctcccac tgcctgtctg tcgtctttgc cagtatctct ctcgcgctct     120
gcctctcacc cttcccctta actgcgcag gcc tgc aca gac ctg ctt tcg cac      173
                                 Ala Cys Thr Asp Leu Leu Ser His
                                   1               5 cag aag cag ctc acc gtg ggc ctg ccg ccc gag ccc cgg gag aag atc      221
Gln Lys Gln Leu Thr Val Gly Leu Pro Pro Glu Pro Arg Glu Lys Ile
     10              15                  20 atc tct gc gtaagtcctc agccttgggg acctcaggtt tgcggggag ccatggggaa     279
Ile Ser
 25 aacagcgctt cccagtgttc ggaggagggg cttttaaag aca                       322

<210> SEQ ID NO 22
<211> LENGTH: 243
<212> TYPE: DNA
<213> ORGANISM: Homo sapiens
<220> FEATURE:
<221> NAME/KEY: CDS
<222> LOCATION: (112)...(190)

<400> SEQUENCE: 22
ctctgtcaca tggatgcgtc tagcacagaa ataaggtg ttccatggag ggcgaggagg       60
cactgtctca agacacctca tgcacattcg tgacacaatg ctccttcta g gcc cct     117
                                                        Ala Pro
                                                          1 tcc ccc aga gga gct cac aaa act cat cta cga ggc cag tgg gca gga      165
Ser Pro Arg Gly Ala His Lys Thr His Leu Arg Gly Gln Trp Ala Gly
      5                  10                  15 cat cag cat tgc cgt cct cac gca g gtctggggct ggtgtgggag gggtcgggcc   220
His Gln His Cys Arg Pro His Ala
       20                  25 acagccttcc tcagagtgga ggg                                            243

<210> SEQ ID NO 23
<211> LENGTH: 413
<212> TYPE: DNA
<213> ORGANISM: Homo sapiens
<220> FEATURE:
<221> NAME/KEY: CDS
<222> LOCATION: (225)...(326)

<400> SEQUENCE: 23
acatcatgtg tctaagaatt aagcagatac atgatttaaa cggcagcatt tagaatcccc     60
acggaacagt gcatttcagc cccaaagcaa tagtgaggtt ctcctgaaca ggggacctg    120 ccatggcatc tgctatcacc tccctcccca cccacgtcca cctgaccta cctttacccg    180 ccaccagccc tgtgtttggg acacttacaa gatatttgtt tta gga gaa gag         233
                                                Gly Glu Glu
                                                  1 gct tct gaa agt ttg atg aac ctc agc cct ttc gat atg aaa aat ctc      281
Ala Ser Glu Ser Leu Met Asn Leu Ser Pro Phe Asp Met Lys Asn Leu
      5                  10                  15 ctg cac cat att cta agt ggg aaa gag ttt ggc gtt gaa aga agt          326
Leu His His Ile Leu Ser Gly Lys Glu Phe Gly Val Glu Arg Ser
 20                  25                  30 ggtaagttcc atgctcctgt taacgtcttc agggagctgc ctcctttaca tgcagcagac   386
attagaacca gcactgtggg gcatacg                                       413
```

```
<210> SEQ ID NO 24
<211> LENGTH: 261
<212> TYPE: DNA
<213> ORGANISM: Homo sapiens
<220> FEATURE:
<221> NAME/KEY: CDS
<222> LOCATION: (148)...(177)

<400> SEQUENCE: 24
cccactaaat ggagtccatg atgcactcat gggtcacccc ctgcggtttg accaacacgg      60
ccctggatta agagagaggg caatagaaga agcacgcgtt cttggctcaa agctggtttt     120
gatttcctga tgtatttttg ctttcag atg act agg cgg ttt agt gct gat gaa    174
                               Met Thr Arg Arg Phe Ser Ala Asp Glu
                                 1               5 cag gtgacacccc tttgccttgt tcgtcctttta cttcctgttc tttctggctt           227
Gln
 10 gaatgtggaa agtgaggctg tgactccgca gcat                                 261

<210> SEQ ID NO 25
<211> LENGTH: 210
<212> TYPE: DNA
<213> ORGANISM: Homo sapiens
<220> FEATURE:
<221> NAME/KEY: CDS
<222> LOCATION: (91)...(144)

<400> SEQUENCE: 25
gggtttcgga tgctgactcc atgaccctcc tctctgctgt gtctcttggt gtcattgctg      60
tcaactgagt ggattctttt tgttttgtag  ttc ttt tct gtg ggc cag gcc gcg    114
                                 Phe Phe Ser Val Gly Gln Ala Ala
                                   1               5 tcc agc agt gcg cat tcc tcc aag tct gcg gtaacagtgc ctcgggatta         164
Ser Ser Ser Ala His Ser Ser Lys Ser Ala
        10                  15 ttgtgtccgt ccccgctcct cctcgcgtcc ttcctcatgc tcccac                    210

<210> SEQ ID NO 26
<211> LENGTH: 363
<212> TYPE: DNA
<213> ORGANISM: Homo sapiens
<220> FEATURE:
<221> NAME/KEY: CDS
<222> LOCATION: (90)...(260)

<400> SEQUENCE: 26
gttcgcaagg gccgcccttc gagatggcgc actttccctg gggcacctgg ctgcgtggct      60
tctgaggccc caagctgtct gtcttgcag agg tcc agc acc cca tcc tcg ccc      113
                                Arg Ser Ser Thr Pro Ser Ser Pro
                                  1               5 act ggc acg tca tcc tca gac tcg gga gga cat cac atc ggc tgg ggt      161
Thr Gly Thr Ser Ser Ser Asp Ser Gly Gly His His Ile Gly Trp Gly
        10                  15                  20 gag cgg cag ggc cag tgg ctg cgc agg aga agg ctg gat ggg gcc atc      209
Glu Arg Gln Gly Gln Trp Leu Arg Arg Arg Arg Leu Asp Gly Ala Ile
 25                  30                  35                  40 aac agg gtc ccc gtg gga ttc tac cag agg gtg tgg aag atc ctc cag      257
Asn Arg Val Pro Val Gly Phe Tyr Gln Arg Val Trp Lys Ile Leu Gln
                45                  50                  55 aag gtaagccgag acgcgagctc ctggggaagt gaaccgtccc cttactgtcc            310
```

Lys tggcaaggca tggtggcacc tccaggcgag caaacacaca gccctgagga tgg    363

<210> SEQ ID NO 27
<211> LENGTH: 337
<212> TYPE: DNA
<213> ORGANISM: Homo sapiens
<220> FEATURE:
<221> NAME/KEY: CDS
<222> LOCATION: (122)...(217)

<400> SEQUENCE: 27
ctttgccctg tgtctgaact ctaatctgtt gccatgagag ctttttttct atgttgcacc    60
gctgttacag caatcatgac cagacctcct tcctgccatg gatgatgggg ctgttttcca    120 g gtc caa gaa tac cga gag gcc ctg gag gga ata ctc atc aga ggc aag    169
  Val Gln Glu Tyr Arg Glu Ala Leu Glu Gly Ile Leu Ile Arg Gly Lys
  1               5                  10                  15 aat ggg atc cgc ctg gtg cct gaa ctc tac gct gtc ccg cct aac aag    217
Asn Gly Ile Arg Leu Val Pro Glu Leu Tyr Ala Val Pro Pro Asn Lys
            20                  25                  30 gtaacccagt ggcagagggc cctttgcacc gcttatctag aaataagtga ctcattgctt    277
ggcctgttgg tattctttat cccctttttc gaactaatga acactttttc tccaaactcc    337

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
ctcacagcct tagtcggttc    20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ctgctccgca tctccccgag    20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
atgttatccc gcacccaggc    20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
cacggccagg atactgtaga    20

```
<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ctgctccagc tcgtaggcct                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tgctctgagt gtgtttgaac                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ggccaggaac aggaggaaga                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ttccataatc agcgacttta                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tgagttcagc agggtcataa                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gtattccctc cagggcctct                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 38
ggaactcggt ctactgtgtg                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ccacagatga ggcaccttcc                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gagctgagga tgtacaagga                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
cctctgccaa cagcgagctg                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
tttaagggat cgatttcacc                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ttctatttaa gggatcgatt                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
aaatcttcta tttaagggat                                               20

<210> SEQ ID NO 45
```

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
acatcaggtt tgactgaagt                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ctacaacatc aggtttgact                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
tttcctcaat aagtccttaa                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ccgcgatact ctggacgttc                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gcatatatgt gactaagaat                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ggccaggtag aagtgatgct                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
tcctccagca ggtgcacagg        20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ttactctggc tcctccaaaa        20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
acgatgtggt gagaaattcc        20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
tggctttctt gattacaggt        20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
atcacagaaa gtatgtcccg        20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
caagattcag tgatttacgg        20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
tttcaggaac cttttctagg        20

<210> SEQ ID NO 58
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 58
cagcttctca cagtccacgt                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gtctgcttgg tcctgtaggt                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
agaatgtctg cttggtcctg                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tgtacagaat gtctgcttgg                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
aagaatgtac agaatgtctg                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cataaagaat gtacagaatg                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ctgtgcaggc ctcagccagg                                               20
```

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
agttcaggct ccgtgccagc                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tctgttaatg ccactcctct                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
catttcactc ctcagtctgt                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ggtcatctct cgggtcgtcg                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
accaattgac acctggtcct                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
attcctgtgg cttggtcttt                                               20

<210> SEQ ID NO 71
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 71
aaaagaagtg gcagattcct                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
cgctgtcata aaagaagtgg                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tgcaaataag aagccactgc                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ggtgagaccc tattgcatct                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tggcgtctca gttccctctg                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
tttctgtaac tctctgcaag                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
aaactatttc tgtaactctc                                               20
```

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
agacacaagt gttctatttg                                          20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
aggagaaaac cctagttcat                                          20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
aggaggctgg gtaaacggcc                                          20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
catgggagcc attttaaaca                                          20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
catccttcac gcagtccctg                                          20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
tttccggatt gtcactcctt                                          20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 84
aatgcaagag gctattacct                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cgaatacggt tgccaatttt                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
gcttacctgg agcttagaaa                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
atgactaatg cttacctgga                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
agaagggcac cagcatgact                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gatgaaacag ttgaggaaag                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cctttccaat attccaacat                                              20

<210> SEQ ID NO 91
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 91
taaattcttg cataaccta                                             20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
ccttagtcgg ttcttgggat                                            20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
agaaccgaga tgcccccatg                                            20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
aacagagata aatgccagcc                                            20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
cacaatagtg accatgggca                                            20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tcctccgaac actgggaagc                                            20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
```
ggagcattgt gtcacgaatg                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ctccactctg aggaaggctg                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
aacttaccac ttctttcaac                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
tctattgccc tctctcttaa                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
cttcttctat tgccctctct                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
ataatcccga ggcactgtta                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
ggaaagtgcg ccatctcgaa                                              20

<210> SEQ ID NO 104
<211> LENGTH: 20
<212> TYPE: DNA
<213> ORGANISM: Artificial Sequence -continued

```
<220> FEATURE:
<223> OTHER INFORMATION: Antisense Oligonucleotide

<400> SEQUENCE: 104
cccagggaaa gtgcgccatc                                              20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
ctgccactgg gttaccttgt                                              20
```

US 6,458,591 B1

ANTISENSE MODULATION OF PHOSPHORYLASE KINASE ALPHA 2 EXPRESSION

FIELD OF THE INVENTION

The present invention provides compositions and methods for modulating the expression of Phosphorylase kinase alpha 2. In particular, this invention relates to antisense compounds, particularly oligonucleotides, specifically hybridizable with nucleic acids encoding Phosphorylase kinase alpha 2. Such oligonucleotides have been shown to modulate the expression of Phosphorylase kinase alpha 2.

BACKGROUND OF THE INVENTION

Balanced energy metabolism is critical to the regulation of all biological processes. In higher organisms, energy stores are in the form of glycogen. Upon energy deficit, these stores are mobilized through enzymatic digestion to glucose-1-phosphate by a diverse set of signals and are used to maintain blood-glucose levels, as a source of energy during muscle contraction and as source of fuel for a broad range of cellular activities.

The protein kinase, phosphorylase kinase (PHK) plays a central role in the regulation of glycogen degradation or glycogenolysis by phosphorylating glycogen phosphorylase b, a unique reaction catalyzed only by phosphorylase kinase. It also lies at the interface between signaling and metabolic pathways and translates the pleiotropic actions of extracellular signals, including hormonal and neuronal, into specific and directional intracellular responses. In addition, phosphorylase kinase can express varying degrees of activity depending on pH, metal ion concentration, allosteric effectors and covalent modifications (Brushia and Walsh, *Front. Biosci.*, 1999, 4, D618–641).

Structurally, phosphorylase kinase is one of the most complex enzymes isolated to date, a hexadecamer, having three distinct regulatory subunits, alpha, beta and delta (also known as calmodulin), and one catalytic subunit, gamma. Each holoenzyme is composed of four heterotetramers of the component subunits and the subunit stoichiometry has been shown to vary depending on the tissue source. The phosphorylase kinase subunits also exist as multiple isoforms adding an additional layer of complexity. The alpha, beta, and gamma isoforms are expressed in the liver and muscle with minor amounts in the gut, while the delta (calmodulin) isoforms are expressed in all tissues examined (Brushia and Walsh, *Front. Biosci.*, 1999, 4, D618–641).

Due to the direct relationship between phosphorylase kinase enzyme activity and maintenance of blood-glucose homeostasis, modifications to the regulatory properties of this enzyme and/or its subunits could provide great therapeutic benefit in the arena of metabolic disorders, especially diabetes.

Phosphorylase kinase alpha 2 (also known as PHKA2) is the liver-specific isoform of the regulatory alpha subunit. Two genes on the X chromosome encode the alpha subunit, but only one of these is expressed in the liver, giving rise to several alternatively spliced isoforms (Davidson et al., *Proc. Natl. Acad. Sci. U.S.A.*, 1992, 89, 2096–2100). Certain mutations in the phosphorylase kinase alpha 2 gene are known to be responsible for type I and type II X-linked glycogen storage disease (XLGI and XLGII) (Burwinkel et al., *Hum. Mol. Genet.*, 1996, 5, 653–658; Hendrickx et al., *Hum. Mol. Genet.*, 1993, 2, 583–589; Hendrickx et al., *Hum. Mol. Genet.*, 1995, 4, 77–83; Hendrickx et al., *Am. J. Hum. Genet.*, 1999, 64, 1541–1549).

Currently however, there are no known therapeutic agents which effectively inhibit the synthesis of phosphorylase kinase alpha 2 and to date, investigative strategies aimed at studying phosphorylase kinase alpha 2 function have involved the use of antibodies, and cross linking agents.

Consequently, there remains a long felt need for agents capable of effectively modulating phosphorylase kinase alpha 2 function.

Antisense technology is emerging as an effective means for reducing the expression of specific gene products and may therefore prove to be uniquely useful in a number of therapeutic, diagnostic, and research applications for the modulation of phosphorylase kinase alpha 2 expression.

The present invention provides compositions and methods for modulating phosphorylase kinase alpha 2 expression.

SUMMARY OF THE INVENTION

The present invention is directed to antisense compounds, particularly oligonucleotides, which are targeted to a nucleic acid encoding Phosphorylase kinase alpha 2, and which modulate the expression of Phosphorylase kinase alpha 2. Pharmaceutical and other compositions comprising the antisense compounds of the invention are also provided. Further provided are methods of modulating the expression of Phosphorylase kinase alpha 2 in cells or tissues comprising contacting said cells or tissues with one or more of the antisense compounds or compositions of the invention. Further provided are methods of treating an animal, particularly a human, suspected of having or being prone to a disease or condition associated with expression of Phosphorylase kinase alpha 2 by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding Phosphorylase kinase alpha 2, ultimately modulating the amount of Phosphorylase kinase alpha 2 produced. This is accomplished by providing antisense compounds which specifically hybridize with one or more nucleic acids encoding Phosphorylase kinase alpha 2. As used herein, the terms "target nucleic acid" and "nucleic acid encoding Phosphorylase kinase alpha 2" encompass DNA encoding Phosphorylase kinase alpha 2, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Phosphorylase kinase alpha 2. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Phosphorylase kinase alpha 2. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon,". the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Phosphorylase kinase alpha 2, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e. from about 8 to about 30 linked nucleosides). Particularly preferred antisense compounds are antisense oligonucleotides, even more preferably those comprising from about 12 to about 25 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples hereinbelow.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 31 terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., Tetrahedron Lett., 1995, 36, 3651–3654), a palmityl moiety (Mishra et al., Biochim. Biophys. Acta, 1995, 1264, 229–237), or an octadecylamine or hexylamino-carbonyloxycholesterol moiety (Crooke et al., J. Pharmacol. Exp. Ther., 1996, 277, 923–937.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Phosphorylase kinase alpha 2 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Phosphorylase kinase alpha 2, enabling sandwich and other assays to easily be constructed to exploit this fact. Hybridization of the antisense oligonucleotides of the invention with a nucleic acid encoding Phosphorylase kinase alpha 2 can be detected by means known in the art. Such means may include conjugation of an enzyme to the oligonucleotide, radiolabelling of the oligonucleotide or any other suitable detection means. Kits using such detection means for detecting the level of Phosphorylase kinase alpha 2 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside G$_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, 2C$_{12}$15G, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, 1-monocaprate, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham MA or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling, Va. or ChemGenes, Needham, Mass.).

2'-Fluoro Amidites
2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites 2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of CHCl₃. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH₃CN (700 mL) and set aside. Triethylamine (189 ML, 1.44 M) was added to a solution of triazole (90 g, 1.3 M) in CH₃CN (1 L), cooled to −5° C. and stirred for 0.5 h using an overhead stirrer. POCl₃ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO₃ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH₄OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH₃ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl₃ (700 mL) and extracted with saturated NaHCO₃ (2×300 mL) and saturated NaCl (2×300 mL) dried over MgSO₄ and evaporated to give a residue (96 g). The residue was chromatographed on a 1.5 kg silica column using EtOAc/hexane (1:1) containing 0.5% Et₃NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH₂Cl₂ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO₃ (1×300 mL) and saturated NaCl (3×300 mL). The aqueous washes were back-extracted with CH₂Cl₂ (300 mL), and the extracts were combined, dried over MgSO₄ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl)nucleoside amidites and 2'-O-(dimethylaminooxyethyl)nucleoside Amidites 2'-(Dimethylaminooxyethoxy)nucleoside Amidites 2'-(Dimethylaminooxyethoxy)nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O²-2'-anhydro-5-methyluridine

O²-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O²-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-Phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-Butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirrred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(Dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(Dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

b 5'-O-DMT-2'-O-(2-N,N-Dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy)nucleoside Amidites

2'-(Aminooxyethoxy)nucleoside amidites [also known in the art as 2'-O-(aminooxyethyl)nucleoside amidites] are prepared as described in the following paragraphs. Adenosine, cytidine and thymidine nucleoside amidites are prepared similarly.

N2-Isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-Dimethylaminoethoxyethoxy (2'-DMAEOE) nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-Dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-Dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.
5'-O-Dimethoxytrityl-2'-O-[2(2-N,N-dimethylaminoethoxy)-ethyl)]-5-methyl Uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3,-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "awing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphor amidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(Methoxyethyl)]Chimeric Phosphorothioate Oligonucleotides

[2'-O-(2-methoxyethyl)]—[2'-deoxy]—[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester]Chimeric Oligonucleotides

[2'-O-(2-methoxyethyl phosphodiester]—[2'-deoxy phosphorothioate]—[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide. ps A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10
Analysis of Oligonucleotide Inhibition of Phosphorylase Kinase Alpha 2 Expression Antisense modulation of Phosphorylase kinase alpha 2 expression can be assayed in a variety of ways known in the art. For example, Phosphorylase kinase alpha 2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target. gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Protein levels of Phosphorylase kinase alpha 2 can be quantitated in a variety of ways well known in the art, such as immunoprecipitation, Western blot analysis (immunoblotting), ELISA or fluorescence-activated cell sorting (FACS). Antibodies directed to Phosphorylase kinase alpha 2 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11
Poly(A)+ mRNA Isolation

Poly(A)+ mRNA was isolated according to Miura et al., Clin. Chem., 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine, Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12
Total RNA Isolation

Total mRNA was isolated using an RNEASY $_{96}$™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 100 µL Buffer RLT was added to each well and the plate was vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia, Calif.). Essentially, after lysing of the cells on the culture plate, the plate is transferred to the robot deck where the pipetting, DNase treatment and elution steps are carried out.

Example 13
Real-time Quantitative PCR Analysis of Phosphorylase Kinase Alpha 2 mRNA Levels Quantitation of Phosphorylase kinase alpha 2 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 µL PCR cocktail (1×TAQMAN™ buffer A, 5.5 mM MgCl$_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL poly(A)

mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Probes and primers to human Phosphorylase kinase alpha 2 were designed to hybridize to a human Phosphorylase kinase alpha 2 sequence, using published sequence information (GenBank accession number X80497, incorporated herein as SEQ ID NO:3). For human Phosphorylase kinase alpha 2 the PCR primers were:

forward primer: TGGAGGACGCAAGTCAGTGA (SEQ ID NO: 4)
reverse primer: CGACGCTCTTGGCAGCAT (SEQ ID NO: 5) and the PCR probe was: FAM-AGATGAGGTCGAGCACTGCCAGTCTATTCTG-TAMRA (SEQ ID NO: 6) where FAM (PE-Applied Biosystems, Foster City, Calif.) is the fluorescent reporter dye and TAMRA (PE-Applied Biosystems, Foster City, Calif.) is the quencher dye. For human GAPDH the PCR primers were:
forward primer: GAAGGTGAAGGTCGGAGTC (SEQ ID NO: 7)
reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Phosphorylase Kinase Alpha 2 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Phosphorylase kinase alpha 2, a human Phosphorylase kinase alpha 2 specific probe was prepared by PCR using the forward primer TGGAGGACGCAAGT-CAGTGA (SEQ ID NO: 4) and the reverse primer CGACGCTCTTGGCAGCAT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Phosphorylase Kinase Alpha 2 Expression by Chimeric Phosphorothioate Oligonucleotides having 2'-MOE Wings and a Deoxy Cap In accordance with the present invention, a series of oligonucleotides were designed to target different regions of the human Phosphorylase kinase alpha 2 RNA, using published sequences (GenBank accession number X80497, incorporated herein as SEQ ID NO: 3, GenBank accession number AF044555, incorporated herein as SEQ ID NO: 10, GenBank accession number AF044541, incorporated herein as SEQ ID NO: 11, GenBank accession number AF044543, incorporated herein as SEQ ID NO: 12, GenBank accession number AF044546, incorporated herein as SEQ ID NO: 13, GenBank accession number AF044547, incorporated herein as SEQ ID NO: 14, GenBank accession number AF044548, incorporated herein as SEQ ID NO: 15, GenBank accession number AF044549, incorporated herein as SEQ ID NO: 16, GenBank accession number D38616, incorporated herein as SEQ ID NO: 17, GenBank accession number AF044553, incorporated herein as SEQ ID NO: 18, GenBank accession number AF044571, incorporated herein as SEQ ID NO: 19, GenBank accession number AF044558, incorporated herein as SEQ ID NO: 20, GenBank accession number AF044562, incorporated herein as SEQ ID NO: 21, GenBank accession number AF044563, incorporated herein as SEQ ID NO: 22, GenBank accession number AF044565, incorporated herein as SEQ ID NO: 23, GenBank accession number AF044567, incorporated herein as SEQ ID NO: 24, GenBank accession number AF044568, incorporated herein as SEQ ID NO: 25, GenBank accession number AF044569, incorporated herein as SEQ ID NO: 26, and GenBank accession number AF044550, incorporated herein as SEQ ID NO: 27). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human Phosphorylase kinase alpha 2 mRNA levels by quantitative real-time PCR as described in other examples herein. Data are averages from two experiments. If present, "N.D." indicates "no data".

TABLE 1

Inhibition of human Phosphorylase kinase alpha 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 118725 | 5'UTR | 3 | 15 | ctcacagccttagtcggttc | 83 | 28 |
| 118726 | Start Codon | 3 | 118 | ctgctccgcatctccccgag | 84 | 29 |
| 118727 | Coding | 3 | 250 | atgttatcccgcacccaggc | 86 | 30 |
| 118728 | Coding | 3 | 269 | cacggccaggatactgtaga | 59 | 31 |
| 118729 | Coding | 3 | 344 | ctgctccagctcgtaggcct | 71 | 32 |
| 118730 | Coding | 3 | 429 | tgctctgagtgtgtttgaac | 66 | 33 |
| 118731 | Coding | 3 | 545 | ggccaggaacaggaggaaga | 0 | 34 |
| 118732 | Coding | 3 | 654 | ttccataatcagcgacttta | 77 | 35 |
| 118733 | Coding | 3 | 1062 | tgagttcagcagggtcataa | 86 | 36 |
| 118734 | Coding | 3 | 1182 | gtattccctccagggcctct | 0 | 37 |
| 118735 | Coding | 3 | 1288 | ggaactcggtctactgtgtg | 86 | 38 |
| 118736 | Coding | 3 | 1313 | ccacagatgaggcaccttcc | 85 | 39 |
| 118737 | Coding | 3 | 1339 | gagctgagqatgtacaagga | 81 | 40 |
| 118738 | Coding | 3 | 1353 | cctctgccaacagcgagctg | 83 | 41 |
| 118739 | Coding | 3 | 1387 | tttaagggatcgatttcacc | 84 | 42 |
| 118740 | Coding | 3 | 1392 | ttctatttaagggatcgatt | 81 | 43 |
| 118741 | Coding | 3 | 1397 | aaatcttctatttaagggat | 60 | 44 |
| 118742 | Coding | 3 | 1420 | acatcaggtttgactgaagt | 79 | 45 |
| 118743 | Coding | 3 | 1425 | ctacaacatcaggtttgact | 75 | 46 |
| 118744 | Coding | 3 | 1478 | tttcctcaataagtccttaa | 82 | 47 |
| 118745 | Coding | 3 | 1506 | ccgcgatactctggacgttc | 80 | 48 |
| 118746 | Coding | 3 | 1558 | gcatatatgtgactaagaat | 62 | 49 |
| 118747 | Coding | 3 | 1706 | ggccaggtagaagtgatgct | 68 | 50 |
| 118748 | Coding | 3 | 1773 | tcctccagcaggtgcacagg | 89 | 51 |
| 118749 | Coding | 3 | 1905 | ttactctggctcctccaaaa | 85 | 52 |
| 118750 | Coding | 3 | 1941 | acgatgtggtgagaaattcc | 83 | 53 |
| 118751 | Coding | 3 | 2077 | tggctttcttgattacaggt | 51 | 54 |
| 118752 | Coding | 3 | 2215 | atcacagaaagtatgtcccg | 83 | 55 |
| 118753 | Coding | 3 | 2304 | caagattcagtgatttacgg | 86 | 56 |
| 118754 | Coding | 3 | 2343 | tttcaggaacctttctagg | 77 | 57 |
| 118755 | Coding | 3 | 2396 | cagcttctcacagtccacgt | 70 | 58 |
| 118756 | Coding | 3 | 2441 | gtctgcttggtcctgtaggt | 73 | 59 |
| 118757 | Coding | 3 | 2446 | agaatgtctgcttggtcctg | 83 | 60 |
| 118758 | Coding | 3 | 2451 | tgtacagaatgtctgcttgg | 70 | 61 |
| 118759 | Coding | 3 | 2456 | aagaatgtacagaatgtctg | 66 | 62 |
| 118760 | Coding | 3 | 2460 | cataaagaatgtacagaatg | 41 | 63 |
| 118761 | Coding | 3 | 2634 | ctgtgcaggcctcagccagg | 53 | 64 |
| 118762 | Coding | 3 | 2907 | agttcaggctccgtgccagc | 48 | 65 |
| 118763 | Coding | 3 | 3113 | tctgttaatgccactcctct | 65 | 66 |
| 118764 | Coding | 3 | 3128 | catttcactcctcagtctgt | 72 | 67 |
| 118765 | Coding | 3 | 3449 | ggtcatctctcgggtcgtcg | 77 | 68 |
| 118766 | Coding | 3 | 3656 | accaattgacacctggtcct | 82 | 69 |
| 118767 | Coding | 3 | 3694 | attcctgtggcttggtcttt | 80 | 70 |
| 118768 | Coding | 3 | 3708 | aaaagaagtggcagattcct | 26 | 71 |
| 118769 | Coding | 3 | 3717 | cgctgtcataaaagaagtgg | 67 | 72 |
| 118770 | Coding | 3 | 3778 | tgcaaataagaagccactgc | 80 | 73 |
| 118771 | Stop Codon | 3 | 3824 | ggtgagaccctattgcatct | 78 | 74 |
| 118772 | 3'UTR | 3 | 4150 | tggcgtctcagttccctctg | 68 | 75 |
| 118773 | 3'UTR | 3 | 4183 | tttctgtaactctctgcaag | 82 | 76 |
| 118774 | 3'UTR | 3 | 4189 | aaactatttctgtaactctc | 46 | 77 |
| 118775 | 3'UTR | 3 | 4320 | agacacaagtgttctatttg | 65 | 78 |
| 118776 | 3'UTR | 3 | 4505 | aggagaaaaccctagttcat | 68 | 79 |
| 118790 | Intron | 10 | 102 | aggaggctgggtaaacggcc | 63 | 80 |
| 118791 | Intron | 10 | 339 | catgggagccatttaaaca | 87 | 81 |
| 118778 | Intron | 11 | 86 | catccttcacgcagtccctg | 10 | 82 |
| 118779 | Intron | 12 | 293 | ttccggattgtcactcctt | 70 | 83 |
| 118780 | 5' splice site | 13 | 227 | aatgcaagaggctattacct | 62 | 84 |
| 118781 | Intron | 14 | 13 | cgaatacggttgccaatttt | 71 | 85 |
| 118782 | Coding | 14 | 256 | gcttacctggagcttagaaa | 70 | 86 |
| 118783 | 5' splice site | 14 | 265 | atgactaatgcttacctgga | 0 | 87 |
| 118784 | Intron | 14 | 279 | agaagggcaccagcatgact | 21 | 88 |
| 118785 | Intron | 15 | 205 | gatgaaacagttgaggaaag | 39 | 89 |
| 118786 | Intron | 15 | 270 | cctttccaatattccaacat | 59 | 90 |
| 118787 | Intron | 16 | 322 | taaattcttgcataaccccta | 61 | 91 |
| 118777 | Intron | 17 | 53 | ccttagtcggttcttgggat | 73 | 92 |
| 118789 | Intron | 18 | 286 | agaaccgagatgcccccatg | 0 | 93 |

TABLE 1-continued

Inhibition of human Phosphorylase kinase alpha 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 118802 | Intron | 19 | 299 | aacagagataaatgccagcc | 0 | 94 |
| 118792 | Intron | 20 | 13 | cacaatagtgaccatgggca | 67 | 95 |
| 118793 | Intron | 21 | 286 | tcctccgaacactgggaagc | 80 | 96 |
| 118794 | Intron | 22 | 85 | ggagcattgtgtcacgaatg | 56 | 97 |
| 118795 | Intron | 22 | 222 | ctccactctgaggaaggctg | 78 | 98 |
| 118796 | Coding | 23 | 315 | aacttaccacttctttcaac | 9 | 99 |
| 118797 | Intron | 24 | 68 | tctattgccctctctcttaa | 45 | 100 |
| 118798 | Intron | 24 | 73 | cttcttctattgccctctct | 68 | 101 |
| 118799 | Intron | 25 | 146 | ataatcccgaggcactgtta | 68 | 102 |
| 118800 | Intron | 26 | 18 | ggaaagtgcgccatctcgaa | 50 | 103 |
| 118801 | Intron | 26 | 23 | cccagggaaagtgcgccatc | 73 | 104 |
| 118788 | Coding | 27 | 213 | ctgccactggttaccttgt | 68 | 105 |

As shown in Table 1, SEQ ID NOs 28, 29, 30, 31, 32, 33, 35, 36, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 72, 73, 74, 75, 76, 77, 78, 79, 80, 81, 83, 84, 85, 86, 89, 90, 91, 92, 95, 96, 97, 98, 100, 101, 102, 103, 104 and 105 demonstrated at least 35% inhibition of human Phosphorylase kinase alpha 2 expression in this assay and are therefore preferred.

Example 16
Western Blot Analysis of Phosphorylase Kinase Alpha 2 Protein Levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Phosphorylase kinase alpha 2 is used, with a radiolabelled or fluorescently labeled secondary antibody directed against the primary antibody species. Bands are visualized using a PHOSPHORIMAGER™ (Molecular Dynamics, Sunnyvale, Calif.).

What is claimed is:

1. An antisense compound 8 to 30 nucleobases in length targeted to nucleobases 250 through 4524 of a coding region, or nucleobases 4150 through 4524 of a 3'-untranslated region of a nucleic acid molecule encoding human Phosphorylase kinase alpha 2 of SEQ ID NO: 3, wherein said antisense compound specifically hybridizes with one of said regions and inhibits the expression of human Phosphorylase kinase alpha 2.

2. The antisense compound of claim 1 which is an antisense oligonucleotide.

3. A antisense compound up to 30 nucleobases in length comprising at least an 8-nucleobase portion of SEQ ID NO: 28, 29, 30, 31, 32, 33, 35, 36, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 72, 73, 74, 75, 76, 77, 78, 79, 80, 81, 83, 84, 85, 86, 89, 90, 91, 92, 95, 96, 97, 98, 100, 101, 102, 103, 104 or 105 which inhibits the expression of human Phosphorylase kinase alpha 2.

4. The antisense compound of claim 2 wherein the antisense oligonucleotide comprises at least one modified internucleoside linkage.

5. The antisense compound of claim 4 wherein the modified internucleoside linkage is a phosphorothioate linkage.

6. The antisense compound of claim 2 wherein the antisense oligonucleotide comprises at least one modified sugar moiety.

7. The antisense compound of claim 6 wherein the modified sugar moiety is a 2'-O-methoxyethyl sugar moiety.

8. The antisense compound of claim 2 wherein the antisense oligonucleotide comprises at least one modified nucleobase.

9. The antisense compound of claim 8 wherein the modified nucleobase is a 5-methylcytosine.

10. The antisense compound of claim 1 wherein the antisense oligonucleotide is a chimeric oligonucleotide.

11. A composition comprising the antisense compound of claim 1 and a pharmaceutically acceptable carrier or diluent.

12. The composition of claim 11 further comprising a colloidal dispersion system.

13. The composition of claim 11 wherein the antisense compound is an antisense oligonucleotide.

14. A method of inhibiting the expression of human Phosphorylase kinase alpha 2 in cells or tissues comprising contacting said cells or tissues in vitro with the antisense compound of claim 1 so that expression of human Phosphorylase kinase alpha 2 is inhibited.

15. The antisense compound of claim 3 which is an antisense oligonucleotide.

16. The antisense compound of claim 15 wherein the antisense oligonucleotide comprises at least one modified internucleoside linkage.

17. The antisense compound of claim 16 wherein the modified internucleoside linkage is a phosphorothioate linkage.

18. The antisense compound of claim 15 wherein the antisense oligonucleotide comprises at least one modified sugar moiety.

19. The antisense compound of claim 18 wherein the modified sugar moiety is a 2'-O-methoxyethyl sugar moiety.

20. The antisense compound of claim 15 wherein the antisense oligonucleotide comprises at least one modified nucleobase.

21. The antisense compound of claim 20 wherein the modified nucleobase is a 5-methylcytosine.

22. The antisense compound of claim 15 wherein the antisense oligonucleotide is a chimeric oligonucleotide.

23. A method of inhibiting the expression of human Phosphorylase kinase alpha 2 in human cells or tissues comprising contacting said cells or tissues in vitro with the antisense compound of claim 3 so that expression of human Phosphorylase kinase alpha 2 is inhibited.

24. A composition comprising the antisense compound of claim 3 and a pharmaceutically acceptable carrier or diluent.

25. The composition of claim 24 further comprising a colloidal dispersion system.

26. The composition of claim 24 wherein the antisense compound is an antisense oligonucleotide.

* * * * *